US00PP27766P3

(12) United States Plant Patent
Stemkens

(10) Patent No.: US PP27,766 P3
(45) Date of Patent: Mar. 7, 2017

(54) ***GAILLARDIA* PLANT NAMED 'GAIZ0001'**

(50) Latin Name: *Gaillardia aristata*
Varietal Denomination: GAIZ0001

(71) Applicant: SYNGENTA PARTICIPATIONS AG, Basel (CH)

(72) Inventor: Henricus Godefridus Wilhelmus Stemkens, Enkuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,307

(22) Filed: Dec. 15, 2015

(65) Prior Publication Data

US 2016/0198617 P1 Jul. 7, 2016

Related U.S. Application Data

(60) Provisional application No. 62/100,124, filed on Jan. 6, 2015.

(51) Int. Cl.
*A01H 5/02* (2006.01)

(52) U.S. Cl.
USPC ..... Plt./431

(58) Field of Classification Search
USPC ..... Plt./431
CPC ..... A01H 5/025
See application file for complete search history.

*Primary Examiner* — Kent L Bell
(74) *Attorney, Agent, or Firm* — Dale Skalla

(57) ABSTRACT

A new *Gaillardia* plant named 'GAIZ0001' particularly distinguished by the large bi-color, purple-red and yellow inflorescences just above the foliage, medium to deep green leaves, medium sized and very well-branched, semi-upright plant habit.

1 Drawing Sheet

Latin name of the genus and species of the plant claimed: *Gaillardia aristata.*

Varietal denomination: 'GAIZ0001'.

BACKGROUND OF THE NEW PLANT

The present invention comprises a *Gaillardia* plant, botanically known as *Gaillardia aristata*, and hereinafter referred to by the variety name 'GAIZ0001'.

'GAIZ0001' is a product of a planned breeding program. The new cultivar has large bi-color, purple-red and yellow inflorescences just above the foliage, medium to deep green leaves, medium sized and very well-branched, semi-upright plant habit.

'GAIZ0001' originated from an open pollination occurring in the summer of 2006 in a controlled environment in Enkhuizen, Netherlands. The female parent was an unpatented plant identified as 'L6001-31', having bi-color, yellow and red inflorescences and a more vigorous and more upright plant habit than 'GAIZ0001'.

The male parent is unknown, because this was an open pollination by a mixture of pollen from the whole population in the trial.

The resulting seeds were sown in Enkhuizen, Netherlands in March 2007. 'GAIZ0001' was selected as one flowering plant, designated 'K9201-7', within the progeny of the stated cross in July 2007.

The first act of asexual reproduction of 'GAIZ0001' was accomplished when vegetative cuttings were propagated from the initial selection in October 2007 in a controlled environment in Enkhuizen, Netherlands.

BRIEF SUMMARY OF THE INVENTION

Horticultural examination of plants grown from cuttings of the plant initiated in the spring of 2008 in Enkhuizen, Netherlands, and continuing thereafter, has demonstrated that the combination of characteristics as herein disclosed for 'GAIZ0001' are firmly fixed and are retained through successive generations of asexual reproduction.

'GAIZ0001' has not been observed under all possible environmental conditions. The phenotype may vary significantly with variations in environment such as temperature, light intensity, and day length.

A Plant Breeder's Right for this cultivar has been applied for with the European Community Plant Variety Office (CPVO) on Oct. 25, 2012, No. 2012/2347; granted on Apr. 22, 2014; No. EU 37713. 'GAIZ0001' has not been made publicly available more than one year prior to the filing of this application.

The following traits have been repeatedly observed and are determined to be basic characteristics of the new variety. The combination of these characteristics distinguishes this *Gaillardia* as a new and distinct variety.

BRIEF DESCRIPTION OF THE PHOTOGRAPHS

The accompanying photographic drawing shows typical inflorescence and foliage characteristics of 'GAIZ0001' with colors being as true as possible with an illustration of this type.

Figure 1:
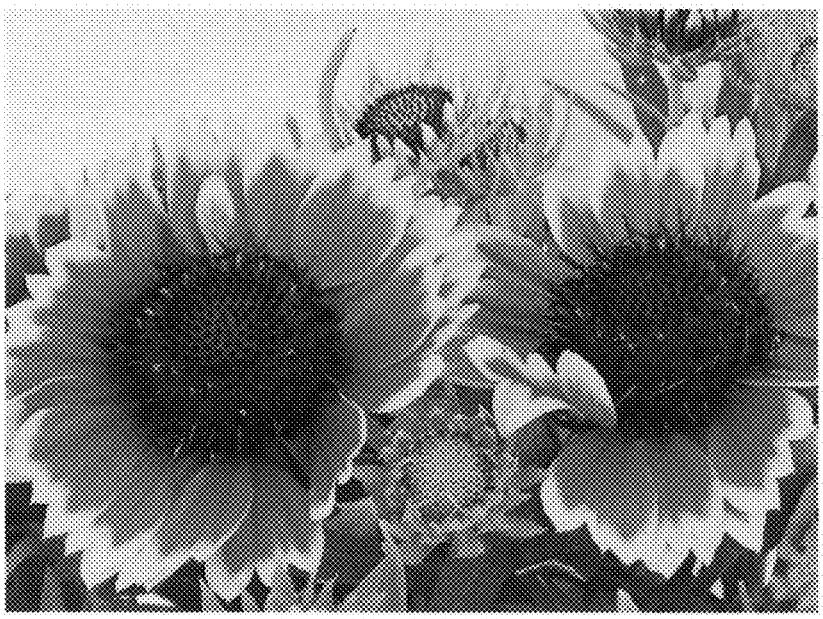
Figure 2:
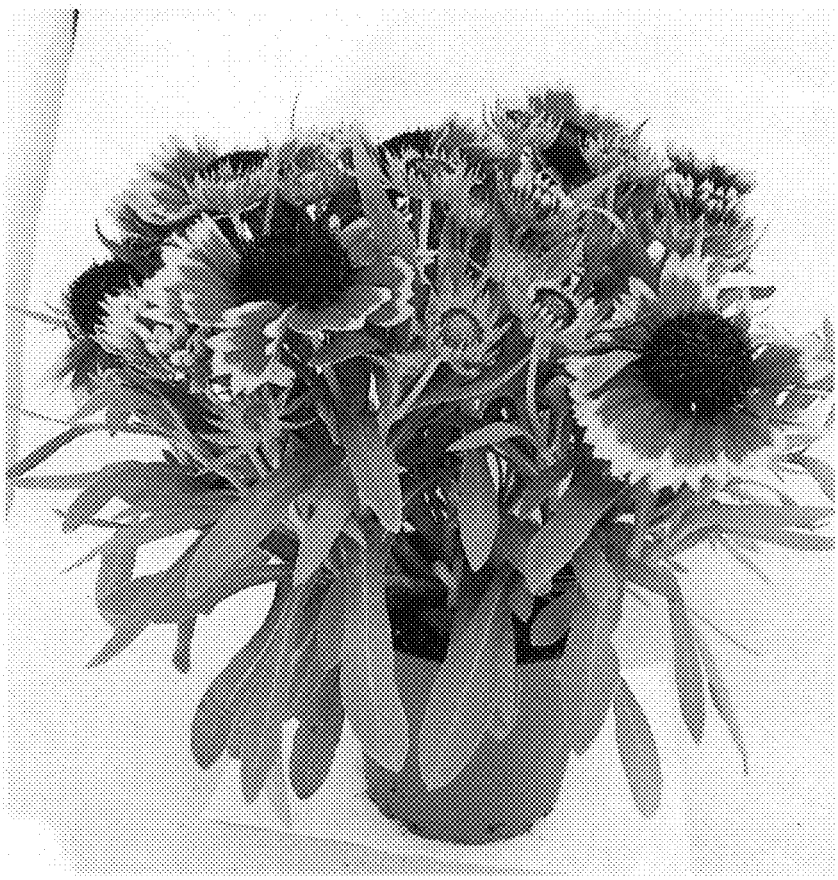

The photographic drawing shows in FIG. 1 a close-up of the inflorescence and in FIG. 2 a whole flowering plant of the new variety.

DETAILED BOTANICAL DESCRIPTION

The aforementioned photographs were taken on July 2012 from plants grown in an outdoor trial in Enkhuizen, Netherlands. These plants were grown in 13 cm pots and were approximately 3 months old.

The plant descriptions and measurements were taken in Enkhuizen, Netherlands on Aug. 18, 2014 using 13-14 week old plants from an outdoor trial field. Cultivation of these plants had started in early June 2014 with planting rooted cuttings into 13 cm pots and growing them on the ground under natural outdoor conditions through the summer months.

Color references are made to The Royal Horticultural Society Colour Chart (R.H.S.) 2001

DIFFERENCES BETWEEN THE NEW VARIETY 'GAIZ0001' AND A SIMILAR VARIETY

| | 'GAIZ0001' | 'Gallo Dark Bicolor' |
|---|---|---|
| Inflorescence head, diameter: | 7.5 cm | 6.5 cm |
| Inflorescence, size: | Very uniform | Range from 5 to 8 cm |
| Color of rays: | Mainly RHS 185A to RHS 185B; Yellow tip about ¼ to ⅓ of the whole length, RHS 14A | Mainly RHS 185C, and up till one third of the length yellow, RHS 17B |

Plant:

*Type*.—Perennial, herbaceous, continuously flowering through the summer months, vernalization not essential for initiating of flowering, hardiness tolerates temperature above minus 10° centigrade (frost).

*Form, growth and habit*.—Short, tight and well-branched, relatively compact and small in size, with the inflorescence heads only a little above the foliage canopy.

*Plant height* (*without inflorescences*).—17 cm.

*Plant height* (*inflorescence included*).—26 cm.

*Plant width*.—30 cm.

Roots:

*Number of days to initiate and develop roots*.—21-25 days at about 22 degrees C.

*Type*.—Fine, fibrous, free branching.

*Color*.—RHS N155B but whiter.

Foliage:

*Arrangement*.—Alternate, simple leaves.

*Immature, leaf color, upper surface*.—RHS 138A.

*Lower surface*.—RHS 138B.

*Mature, leaf color, upper surface*.—RHS 137B.

*Lower surface*.—RHS 138B.

*Length*.—7-9 cm.

*Width*.—1.0-1.2 cm.

*Shape*.—Lanceolate to linear, basal leaves may have 3 to 4 lobes.

*Base shape*.—Attenuate.

*Apex shape*.—Acute.

*Margin*.—Mainly entire, margins of basal leaves have some lobes.

*Texture, both surfaces*.—Covered with pubescence, with single longer hairs and upright hair along the edges and on the midrib on the lower surface.

*Color of veins, upper surface*.—RHS 144A to RHS 144B, near base RHS 138B.

*Color of veins, lower surface*.—RHS 144A, near base RHS 138A.

*Petiole color*.—Sessile, no petiole.

Stem:

*Quantity of main branches per plant*.—21-27, each with 1 to 3 secondary branches.

*Color of stem*.—RHS 144B.

*Stem length*.—About 10.0 cm.

*Stem diameter* (*at mid portion*).—0.5 cm.

*Length of internodes* (*at mid portion*).—1.5-3.0 cm mostly.

*Texture*.—Slightly grooved, pilose with relatively long hairs, 0.25 cm, of medium density.

Peduncle:

*Color of peduncle*.—RHS 144B.

*Length of peduncle*.—About 9-9.5 cm.

*Peduncle diameter*.—0.25-0.3 cm.

*Texture*.—Covered with very fine pubescence and with single longer hairs.

Inflorescence:

*Type*.—Capitulum (compositae-type), single inflorescences borne terminally on short peduncles close to or above the foliage.

*Quantity of inflorescences per plant*.—Approximately 50 heads and buds.

*Lastingness of individual blooms on the plant*.—About two weeks depending on temperature.

*Fragrance*.—None.

Bud (just when opening/showing color):

*Color*.—RHS 1B and RHS 143C.

*Length*.—1-1.5 cm.

*Width*.—3 cm.

*Shape*.—Cup-shaped.

*Texture*.—Covered with fine pubescence and with long hair at the base.

Young inflorescence:

*Diameter*.—About 3.2 cm.

*Color of ray floret, upper surface*.—RHS 185A mainly, at the tip RHS 14A.

*Color of rays, lower surface*.—RHS 185C and RHS 14A near tip.

*Color of 'disc' with the disc florets still closed*.—RHS 187B for the outer whorls, and RHS 151 B in the center of the disc.

Mature inflorescence:

*Shape*.—Uniform, large (in relation to plant size), daisy-type inflorescences with one to two whorls of ray florets surrounding the disc, horizontally directed.

*Diameter of whole inflorescence*.—6.0-6.5 cm.

*Diameter of the disc*.—2.7 cm.

*Diameter of the receptacle*.—Approximately 1.5 cm.

Ray florets:

*Average quantity of ray florets*.—15-18, in one to two whorls.

*Overall color*.—Purple-red to deep orange-red for approximately two thirds of the length, and yellow for the apex.

*Color of floret, upper surface*.—RHS 185A to RHS 185B or RHS N34A, turning brighter from base towards the distal end; and yellow, RHS 14A, at the tip.

*Color of lower surface*.—RHS 185C, and RHS 13A at apex.

*Length*.—2.5 cm.

*Width*.—1.4-1.5 cm.

*Shape*.—Ligulate to weakly oblanceolate.

*Apex shape*.—Mostly tri-dentate, sometimes bi-dentate.

*Margin*.—Entire.

*Texture, upper surface*.—Glabrous.

*Texture, lower surface*.—Covered with fine pubescence, slightly protruding veins.

Disc florets:

*Average quantity of disc florets*.—About 80.

*Shape*.—Tube-shaped.

*Apex shape*.—5-pointed with acute tips.

*Color of young disk florets* (*just before opening*), *at apex*.—RHS 187A, purple red.

*Color of open floret*.—RHS 17B at apex, corolla of RHS 187A to RHS 187C.

*Length of floret*.—0.7 cm.

*Width at apex*.—0.3 cm.

Involucre/receptacle:

*Shape*.—Flattened semi-sphere, formed by the phyllaries in an overlapping arrangement.

*Diameter* (*width*).—3.5 cm.

*Diameter* (*depth*).—1.5 cm.

Phyllaries:

*Quantity of phyllaries*.—25-30.

*Shape*.—Lanceolate.

*Apex shape*.—Acuminate.

*Base*.—Sessile, fused with the receptacle.

*Margins*.—Entire.

*Color, outer surface*.—RHS 147B.

*Color, inner side*.—RHS 147B.

*Length*.—1.8-2 cm.

*Width*.—0.15-0.3 cm.

*Texture of both surfaces*.—Densely pubescent with some longer hair, mostly on phyllary edges.

Reproductive organs:

*Gynoecium*.—Developed in ray and disc florets.

*Pistil, number per floret*.—One.

*Pistil, length*.—0.7 cm.

*Style color*.—RHS 12A.

*Style length*.—0.5 cm.

*Stigma color*.—RHS 187A.

*Stigma shape*.—Bi-lobed.

*Stigma, length*.—0.7 cm.

*Ovary, length*.—0.1 cm.

*Androecium*.—Present in disc florets only.

*Number of stamen*.—4 per floret.

*Filaments*.—Fused at the middle and lower part.

*Anther, shape*.—Linear, 4 mm in length.

*Anther color*.—RHS 157D at base, main part RHS 17C.

*Pollen amount*.—Moderate.

*Color of pollen*.—RHS 164A.

*Fertility/seed set*.—Has not been observed on this hybrid.

*Disease/pest resistance*.—Has not been observed on this hybrid.

What is claimed is:

1. A new and distinct variety of *Gaillardia* plant named 'GAIZ0001' substantially as illustrated and described herein.

* * * * *